US011478429B2

(12) United States Patent
Louw

(10) Patent No.: US 11,478,429 B2
(45) Date of Patent: *Oct. 25, 2022

(54) CAPSULE WITH INTERNAL DIAPHRAGM AND SOLID INGREDIENTS

(71) Applicant: ComboCap, Inc., New York, NY (US)

(72) Inventor: Tobias Johan Louw, New York, NY (US)

(73) Assignee: ComboCap, Inc., Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/767,036

(22) PCT Filed: Oct. 10, 2016

(86) PCT No.: PCT/US2016/056293
§ 371 (c)(1),
(2) Date: Apr. 9, 2018

(87) PCT Pub. No.: WO2017/062956
PCT Pub. Date: Apr. 13, 2017

(65) Prior Publication Data
US 2018/0296489 A1 Oct. 18, 2018

Related U.S. Application Data

(60) Provisional application No. 62/239,442, filed on Oct. 9, 2015, provisional application No. 62/239,435, filed
(Continued)

(51) Int. Cl.
A61K 31/355 (2006.01)
A61K 35/741 (2015.01)
A61K 36/53 (2006.01)
A61K 36/71 (2006.01)
A61K 9/48 (2006.01)
A61K 45/06 (2006.01)
A61K 31/05 (2006.01)
A61K 31/60 (2006.01)
A61K 47/12 (2006.01)
A61K 31/616 (2006.01)
A61K 31/122 (2006.01)
A61K 31/137 (2006.01)
A61K 31/192 (2006.01)
A61K 35/00 (2006.01)
A61K 31/4458 (2006.01)
A61K 31/01 (2006.01)
A61K 31/201 (2006.01)
A61K 31/202 (2006.01)
A61K 31/203 (2006.01)
A61K 31/375 (2006.01)
A61K 31/525 (2006.01)
A61K 33/06 (2006.01)
(Continued)

(52) U.S. Cl.
CPC ............ *A61K 9/4808* (2013.01); *A61K 9/485* (2013.01); *A61K 9/4858* (2013.01); *A61K 9/4875* (2013.01); *A61K 31/01* (2013.01); *A61K 31/05* (2013.01); *A61K 31/122* (2013.01); *A61K 31/137* (2013.01); *A61K 31/192* (2013.01); *A61K 31/201* (2013.01); *A61K 31/202* (2013.01); *A61K 31/203* (2013.01); *A61K 31/353* (2013.01); *A61K 31/355* (2013.01); *A61K 31/375* (2013.01); *A61K 31/4458* (2013.01); *A61K 31/525* (2013.01); *A61K 31/60* (2013.01); *A61K 31/616* (2013.01); *A61K 33/06* (2013.01); *A61K 33/18* (2013.01); *A61K 33/26* (2013.01); *A61K 33/42* (2013.01); *A61K 35/741* (2013.01); *A61K 36/53* (2013.01); *A61K 36/71* (2013.01); *A61K 45/06* (2013.01); *A61K 47/12* (2013.01); *A61K 2035/115* (2013.01)

(58) Field of Classification Search
None
See application file for complete search history.

(56) References Cited

U.S. PATENT DOCUMENTS 1,510,260 A 9/1924 Cyrenius
3,066,501 A * 12/1962 Charles ................ A44C 11/002
63/39
(Continued)

FOREIGN PATENT DOCUMENTS

EP 2777802 A1 9/2014
NL 7610038 A 3/1978
(Continued)

OTHER PUBLICATIONS

Extended European Search Report for European Patent Application No. 16854535.8 dated Apr. 2, 2019.
Extended European Search Report for European Patent Application No. 16854536.6 dated Apr. 3, 2019.
Extended European Search Report for European Patent Application No. 16854537.4 dated Mar. 29, 2019.
International Search Report and Written Opinion for PCT/US2016/056276 dated Jan. 10, 2017.
(Continued)

*Primary Examiner* — Robert A Wax
*Assistant Examiner* — Caralynne E Helm
(74) *Attorney, Agent, or Firm* — DLA Piper LLP

(57) ABSTRACT

A two-compartment capsule includes a body, a diaphragm between, which seals off the body and provides a first compartment to hold a first dry ingredient, and a cap applied to the body whereby a space between the inner portion of the cap and the diaphragm defines a second compartment for holding a second dry ingredient. This disclosure also provides particular formulations for use in such a capsule. Examples include a probiotic, a digestive enzyme, an expectorant, a bronchodilator, a stool softener, a platelet aggregation inhibitor, a form or derivative of vitamin E, a statin, and aspirin.

15 Claims, 6 Drawing Sheets

Related U.S. Application Data on Oct. 9, 2015, provisional application No. 62/239,454, filed on Oct. 9, 2015.

(51) Int. Cl.
*A61K 33/18* (2006.01)
*A61K 33/26* (2006.01)
*A61K 33/42* (2006.01)
*A61K 31/353* (2006.01)

(56) References Cited

U.S. PATENT DOCUMENTS

| | | | | |
|---|---|---|---|---|
| 3,927,195 | A | * | 12/1975 | Messora .............. A61J 3/071 |
| | | | | 424/454 |
| 4,339,428 | A | * | 7/1982 | Tencza ............... A61K 9/4808 |
| | | | | 424/451 |
| 4,748,058 | A | * | 5/1988 | Craig, Jr. ............ A47G 33/06 |
| | | | | D11/118 |
| 5,223,265 | A | | 6/1993 | Wong |
| 5,387,421 | A | | 2/1995 | Amidon et al. |
| 5,394,980 | A | | 3/1995 | Tsai |
| 7,670,612 | B2 | | 3/2010 | Miller |
| 2003/0199481 | A1 | | 10/2003 | Garavani et al. |
| 2005/0123603 | A1 | | 6/2005 | Dalland et al. |
| 2006/0280794 | A1 | * | 12/2006 | Hamaguchi ......... A61K 9/209 |
| | | | | 424/472 |
| 2007/0212411 | A1 | * | 9/2007 | Fawzy ............... A61K 9/4891 |
| | | | | 424/457 |
| 2007/0259034 | A1 | | 11/2007 | Steele et al. |
| 2008/0213320 | A1 | * | 9/2008 | Eisenstein .......... A61K 9/0056 |
| | | | | 424/400 |
| 2008/0287368 | A1 | | 11/2008 | Yu et al. |
| 2009/0087483 | A1 | * | 4/2009 | Sison ................. A61K 9/4808 |
| | | | | 424/451 |
| 2010/0048704 | A1 | | 2/2010 | Vermeer et al. |
| 2010/0209389 | A1 | | 8/2010 | McInnes et al. |
| 2012/0209339 | A1 | * | 8/2012 | Scodary .............. A61F 2/4405 |
| | | | | 606/86 R |
| 2012/0269868 | A1 | | 10/2012 | Faerstein |
| 2014/0212482 | A1 | | 7/2014 | Miller |
| 2014/0273150 | A1 | * | 9/2014 | Angel ................. C02F 3/342 |
| | | | | 435/186 |
| 2014/0302133 | A1 | | 10/2014 | Van Rooyen et al. |
| 2015/0246768 | A1 | | 9/2015 | Talon |
| 2016/0038425 | A1 | | 2/2016 | Fang et al. |
| 2018/0289625 | A1 | | 10/2018 | Louw |

FOREIGN PATENT DOCUMENTS

| | | |
|---|---|---|
| WO | 2013050973 A1 | 4/2013 |
| WO | 2014202412 A1 | 12/2014 |
| WO | 2017062951 A1 | 4/2017 |
| WO | 2017062954 A1 | 4/2017 |
| WO | 2017062956 A1 | 4/2017 |

OTHER PUBLICATIONS

International Search Report and Written Opinion for PCT/US2016/056285 dated Jan. 10, 2017.
International Search Report and Written Opinion for PCT/US2016/056293 dated Jan. 23, 2017.
Capsugel® capsule size reference 2 pages (Year: 2013).
Physical Properties of Fats and Oils reference www.dgfett.de/material/physikalische_eigenschaften.pdf 29 pages (Year: 2005).
Aspirin safety data sheet 7 pages (Year: 2015).
Cadé Vcaps® Plus Capsules 12 pages (Year: 2012).
Johnson www.merckmanuals.com/home/disorders-of-nutrition/vitamins/overview-of-vitamins# 9pages (year: 2020).

* cited by examiner

CAPSULE WITH INTERNAL DIAPHRAGM AND SOLID INGREDIENTS

CROSS-REFERENCE TO RELATED APPLICATIONS

This application is a U.S. national stage filing under 35 U.S.C. § 371 of International Application No. PCT/US2016/056293, filed Oct. 10, 2016, entitled "Capsule with Internal Diaphragm and Solid Ingredients," which claims priority to and benefit of U.S. Provisional Application Ser. No. 62/239,435, filed Oct. 9, 2015, entitled "Capsule with Volume-Adjustable Internal Diaphragm," U.S. Provisional Application Ser. No. 62/239,454, filed Oct. 9, 2015, entitled "Capsule with Internal Diaphragm for Improved Bioavailability," and U.S. Provisional Application Ser. No. 62/239,442, filed Oct. 9, 2015, entitled "Capsule with Internal Diaphragm and Solid Ingredients," each of which is hereby incorporated herein by reference in its entirety.

SUMMARY

Embodiments described herein are directed to a multi-compartment capsule comprising a body; a diaphragm, having two sidewalls and a bottom, extending into the body and defining a first compartment between an outer surface of the diaphragm and an inner surface of the body; and a cap mounted to an outer surface of the body and opposed to the diaphragm, and defining a second compartment between an inner surface of the diaphragm and the cap; wherein the two sidewalls of the diaphragm extend along the inner surface of the body and are aligned with an open end of the body. In some embodiments, the capsule is a size 00 capsule.

In some embodiments, the first compartment is hermetically sealed. In some embodiments, the one or more solid ingredients comprise a powder, a granule, a semi-solid, a microbead, a beadlet, or a combination thereof.

In some embodiments, the bottom of the diaphragm may be flattened. In some embodiments, the bottom of the diaphragm may be curved. In some embodiments, the bottom of the diaphragm may be substantially or partially flattened.

In some embodiments, the first compartment and the second compartment each have sufficient volume to administer a therapeutically effective dose of an ingredient.

In some embodiments, the one or more solid ingredients comprises a probiotic. The probiotic may be selected from the group consisting of *Lactobacillus acidophilus, Lactobacillus casei, Lactobacillus gasseri, Lactobacillus helveticus, Lactobacillus bulgaricus, Lactobacillus delbrueckii, Lactobacillus plantarum, Lactobacillus paracasei, Lactobacillus salivarius, Lactobacillus reuteri, Lactobacillus rhamnosus, Lactobacillus brevis, Lactobacillus breve, Streptococcus thermophilus, Bifidobacterium infantis, Bifidobacterium lactis, Bifidobacterium longum, Bifidobacterium bifidum, Bifidobacterium coagulans, Bifidobacterium breve, Bifidobacterium animalis, Bifidobacterium subtilis, Saccharomyces boulardi*, and combinations thereof. In some embodiments, the one or more solid ingredients comprises from about 1 million colony forming units (CFUs) to about 100 billion CFUs of a probiotic.

In some embodiments, the one or more solid ingredients comprises a digestive enzyme. The digestive enzyme may be selected from the group consisting of amylase, alpha-amylase, protease, alpha-galactosidase, beta-gulcanase, galactomannase, lactase, lipase, cellulase, hemicellulase, phytase, sucrase, invertase, pectinase, maltase, malt diastase, glucoamylase, xylanase, pullulanase, peptidase and dipeptidyl peptidase IV, *serratia* peptidase, lysozyme, bromelian, papain, and combinations thereof. In some embodiments, the one or more solid ingredients comprises from about 50 mg to about 1000 mg of a digestive enzyme. In some embodiments, the first compartment comprises from about one million CFUs to about 10 billion CFUs of a probiotic, and the second compartment comprises from about 50 mg to about 1000 mg of a digestive enzyme. In some embodiments, the first compartment comprises from about 10 mg to about 1000 mg of a digestive enzyme, and the second compartment comprises from about 1 million CFUs to about 100 billion CFUs of a probiotic.

In some embodiments, the one or more solid ingredients comprises a pharmaceutical agent. In some embodiments, the pharmaceutical agent is selected from the group consisting of aspirin, a statin, ipriflavone, cohosh, castus, coenzyme Q10 (CoQ10), guaifenesin, althea root, antimony pentasulfide, creosote, guaiacolsulfonate, ipecacuanha (syrup of ipecac), levoverbenone, potassium iodide, senega, tyloxapol, ammonium chloride, salbutamol, albuterol, levosalbutamol, levalbuterol, pirbuterol, epinephrine, ephedrine, terbutaline, salmeterol, clenbuterol, formoterol, bambuerol, indacaterol, ephrinesulfate, ticlopidine, clopidogrel, prasugrel, ticagrelor, cilostazol, vorapaxar, trifusal, dipyridamole, a tocotrienol, and combinations thereof. In some embodiments, the one or more solid ingredients comprises aspirin. In some embodiments, the one or more solid ingredients comprises from about 81 mg to about 324 mg of aspirin. In some embodiments, the aspirin may be in an amount of about 10 mg to about 500 mg.

In some embodiments, the one or more solid ingredients comprises a statin. The statin may be selected from the group consisting of atorvastatin, fluvastatin, lovastatin, pitavastatin, pravastatin, rosuvastatin, simvastatin, and combinations thereof. The statin may be in an amount of about 1 mg to about 100 mg. In some embodiments, the statin may be in an amount of about 5 mg to about 40 mg.

DETAILED DESCRIPTION

Figure 1:
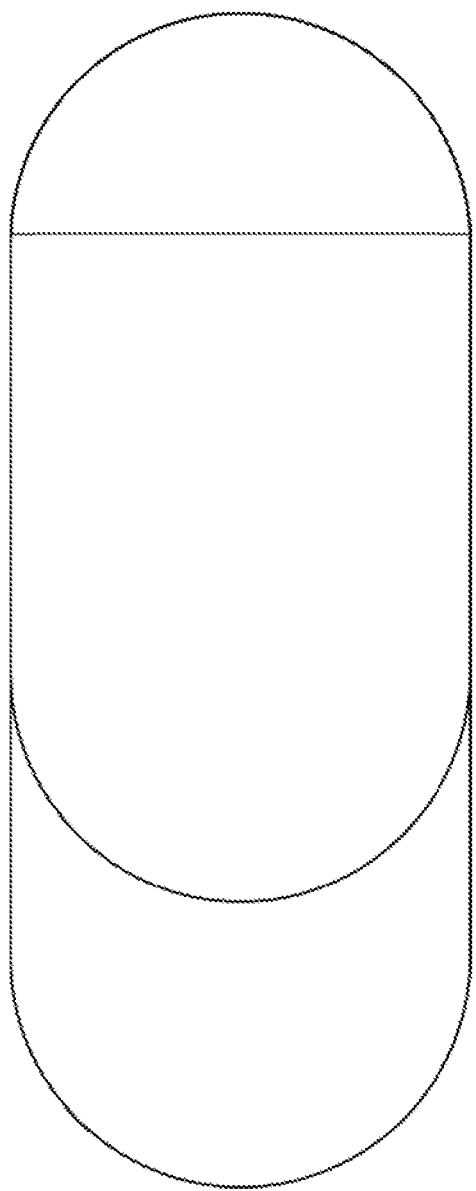
FIG. 1 illustrates a cross-sectional view of a capsule of embodiments herein wherein the first (lower) compartment has a volume of about 423 mm$^3$ and the second (upper) compartment has a volume of about 497 mm$^3$, and wherein each compartment comprises a solid ingredient.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entireties. Nothing herein is to be construed as an admission that the invention is not entitled to antedate such disclosure by virtue of prior invention.

It must also be noted that as used herein and in the appended claims, the singular forms "a," "an," and "the" include plural references unless the context clearly dictates otherwise. Thus, for example, reference to "an ingredient" is a reference to one or more ingredients and equivalents thereof known to those skilled in the art, and so forth.

As used herein, the term "about" means plus or minus 10% of the numerical value of the number with which it is being used. Therefore, about 50 mg means in the range of 45 mg-55 mg.

The term "patient" or "subject" as used herein is an animal, particularly a human, suffering from an unwanted disease or condition that may be treated by the therapeutics and/or compositions described herein.

"Optional" or "optionally" means that the subsequently described event or circumstance may or may not occur, and that the description includes instances where the event occurs and instances where it does not.

Throughout the specification of the application, various terms are used such as "primary," "secondary," "first," "second," and the like. These terms are words of convenience used to distinguish between different elements, and such terms are not intended to limit how the different elements may be used.

As used herein, the term "medicament" or "therapeutic" means an agent used to treat, combat, ameliorate, prevent or improve an unwanted condition or disease of a subject.

A "therapeutically effective amount" or "effective amount" of a composition is an amount necessary or sufficient to achieve the desired result. The activity contemplated by the embodiments herein includes medically therapeutic, cosmetically therapeutic, and/or prophylactic treatment, as appropriate. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

The terms "treat," "treated," or "treating," as used herein, refer to therapeutic treatment, cosmetic treatment, and/or prophylactic or preventative measures, wherein the object is to prevent or slow down (lessen) an undesired physiological condition, disorder, or disease, or to obtain beneficial or desired clinical results. For the purposes of this invention, beneficial or desired clinical results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes eliciting a clinically significant response without excessive levels of side effects.

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition is the specifically recited therapeutic in the particular embodiment or claim.

Capsules are typically manufactured in certain standard sizes, such as TORPAC sizes, referred to as a capsule size designated by numerals, such as 000, 00, etc. Such capsules typically have two parts: a cap and a body, which are bonded or fitted together. One of the most common sizes is the 00 capsule. The typical size 00 capsule, in common with other capsules, has a standardized nominal volume. For instance, a size 00 capsule has a volume of approximately 0.95 milliliters. In some embodiments described below, the multi-compartment capsule is a size 00 capsule. In some embodiments, the capsule size may be size 000, size 0, size 1, size 2, size 3, size 4, or size 5, or any non-standard size in between these sizes. In some embodiments described below, the capsule size may be elongated ("EL"), such that the size may be, for example, 00 EL. In some embodiments, the elongation may be to any standard length or to a non-standard length. In some embodiments, the elongated capsule may add from about 50 mm$^3$ to about 150 mm$^3$ of additional volume to the first compartment, the second compartment, or a combination thereof. In some embodiments, the elongated capsule may add about 110 mm$^3$ of additional volume to the first compartment, the second compartment, or a combination thereof. In some embodiments, if the diaphragm's diameter is reduced, it may be possible to insert a longer diaphragm into the capsule, thereby changing the available volumes in both the first and second compartments. In some embodiments, scaling the dimensions of the multi-compartment capsule described herein may result in a larger or smaller capsule with substantially the same ratios as described herein. In some embodiments, scaling the dimensions of the multi-compartment capsule described herein may result in a larger or smaller capsule with ratios different from those described herein.

For some applications, it may be advantageous to deliver one or more ingredients in the form of a capsule with two compartments. For some applications, it may advantageous for the one or more ingredients delivered in such a capsule to be solid ingredients. Exemplary benefits of such two compartment capsules may include increased compliance, a double chamber controlled release, increased efficacy or bioavailability of ingredients due to co-administration, increased stability, and the ability to formulate difficult combinations of ingredients into one capsule, such as incompatible actives which can now be co-administered.

Embodiments described herein are directed to a multi-compartment capsule comprising a body; a diaphragm, having two sidewalls and a bottom, extending into the body and defining a first compartment between an outer surface of the diaphragm and an inner surface of the body; and a cap mounted to an outer surface of the body and opposed to the diaphragm, and defining a second compartment between an inner surface of the diaphragm and the cap; wherein the two sidewalls of the diaphragm extend along the inner surface of the body and are aligned with an open end of the body. In some embodiments, the capsule is a size 00 capsule.

In some embodiments, the multi-compartment capsule may comprise a body; a diaphragm, having two sidewalls and a bottom, extending into the body and forming a first compartment defined by a first surface of the diaphragm and the body; and a cap mounted to the body and opposed to the diaphragm, the cap forming a second compartment defined by an opposing surface of the diaphragm and the cap; wherein the two sidewalls of the diaphragm extend along the inner surface of the body and are aligned with an open end of the body; and wherein the first compartment and the second compartment are each adapted to hold one or more solid ingredients. In some embodiments, the first compartment is hermetically sealed. In some embodiments, the one or more solid ingredients comprises a powder, a granule, a semi-solid, a microbead, a beadlet, or a combination thereof.

In some embodiments, the bottom of the diaphragm may be flattened. A flatter bottom may allow for more volume in the lower compartment. In some embodiments, the bottom of the diaphragm may be curved. In some embodiments, the bottom of the diaphragm may be substantially or partially flattened.

In some embodiments, the first compartment comprises a solid ingredient. In some embodiments, the second compartment comprises a solid ingredient. In some embodiments, the first compartment and second compartment each comprise one or more solid ingredients. In some embodiments, the first compartment and the second compartment each have sufficient volume to administer a therapeutically effective dose of one or more ingredients.

Figure 2:
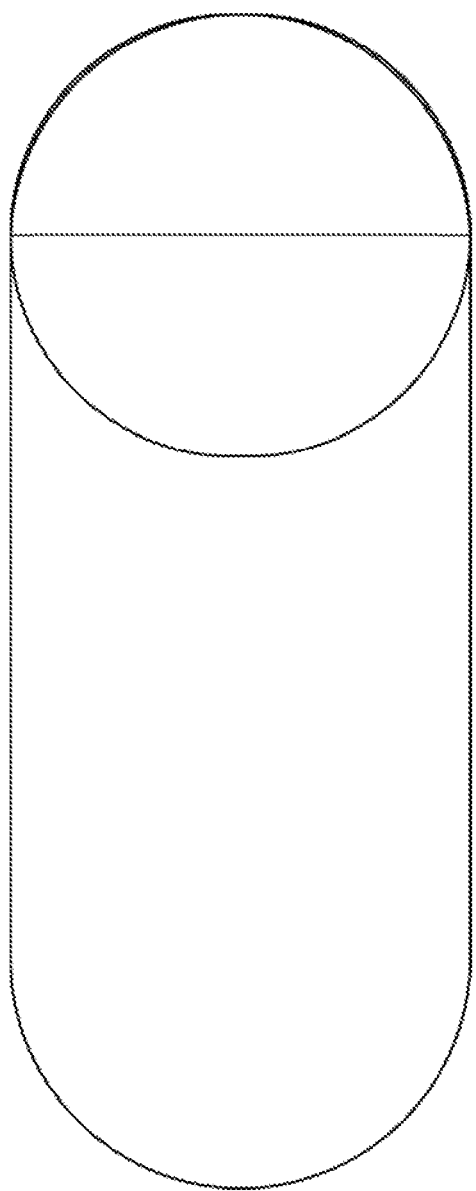
FIG. 2 illustrates a cross-sectional view of a capsule of embodiments herein wherein the first (lower) compartment has a volume of about 743 mm$^3$ and the second (upper) compartment has a volume of about 176 mm$^3$, and wherein each compartment comprises a solid ingredient.
Figure 3:
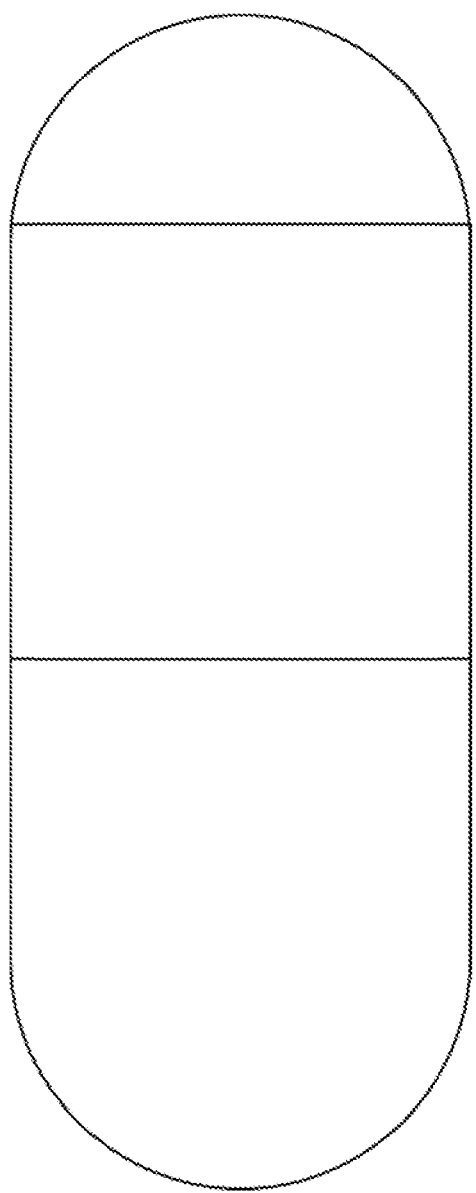
FIG. 3 illustrates a cross-sectional view of a capsule of embodiments herein with a flattened bottom, wherein each compartment comprises a solid ingredient.
Figure 4A:
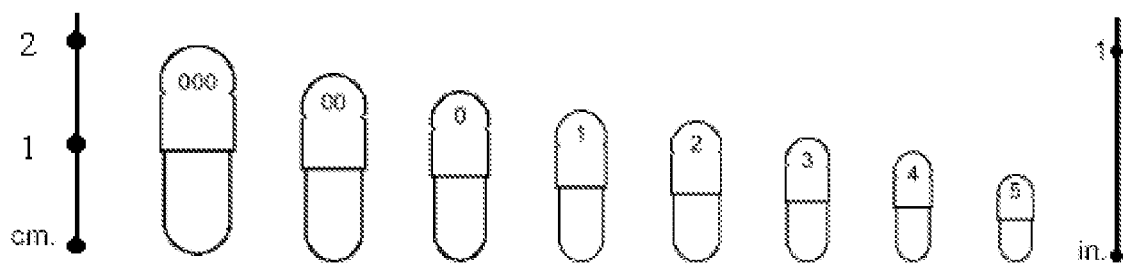
FIGS. 4A, 4B, and 4C illustrate standard and elongated TORPAC capsule sizes, which may be used in some embodiments described herein.
Figure 4B:
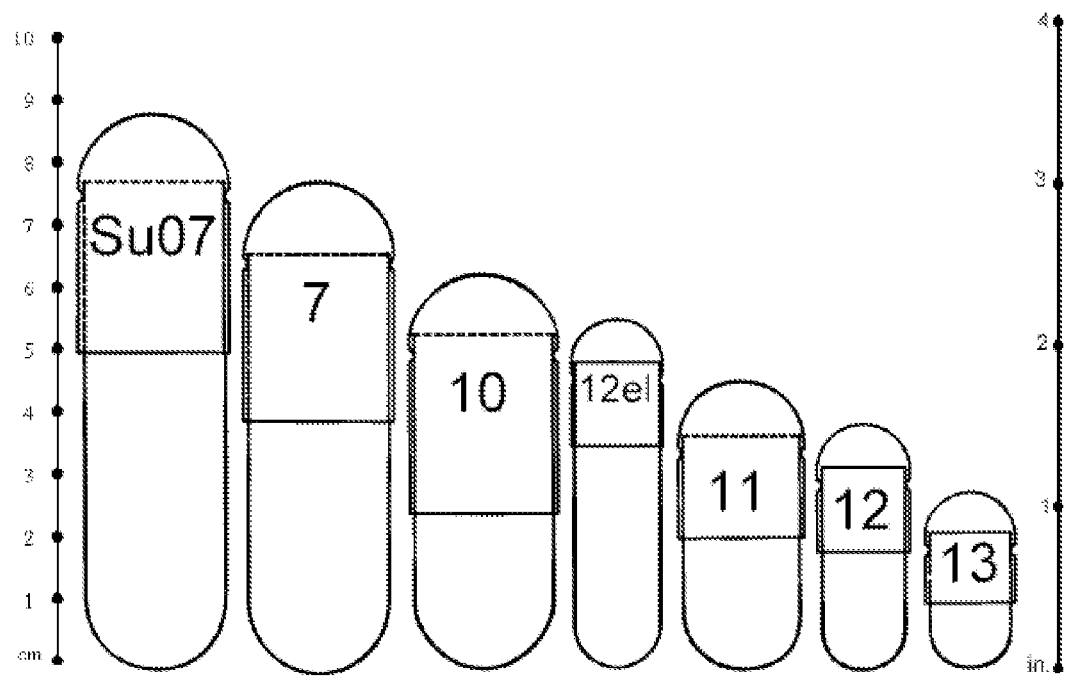
Figure 4C:
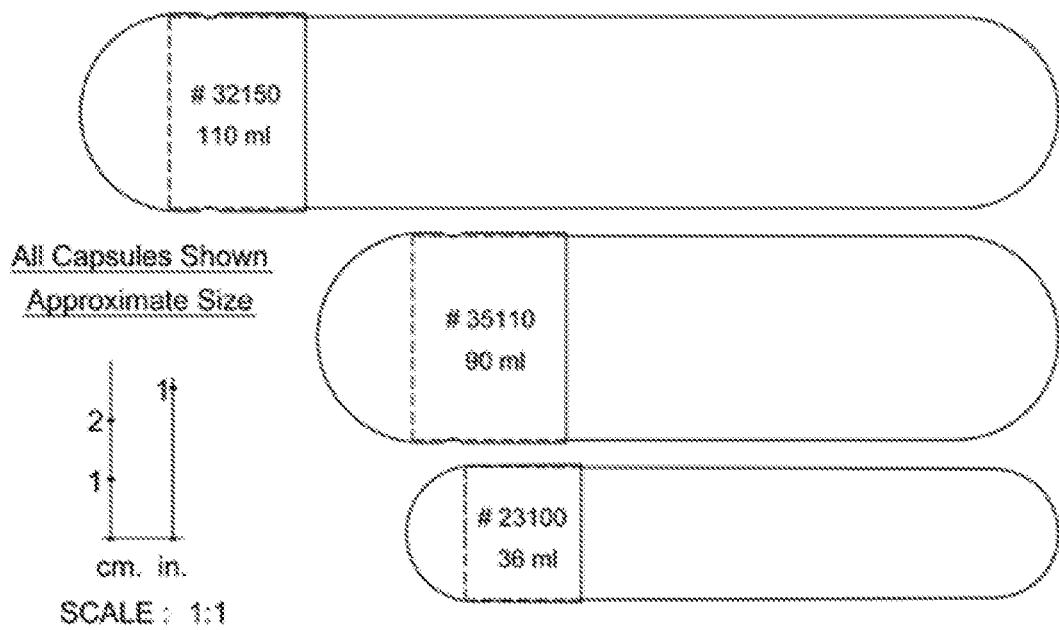

In some embodiments, the first compartment may have a volume of about 50 mm$^3$ to about 1000 mm$^3$, and the second compartment may have a volume of about 50 mm$^3$ to about 1000 mm$^3$. For example, as shown in FIG. 1, a capsule of an embodiment herein may have a first (lower) compartment having a volume of about 423 mm$^3$ and a second (upper) compartment having a volume of about 497 mm$^3$. In some embodiments, as shown in FIG. 2, a capsule of an embodiment herein may have a the first (lower) compartment having a volume of about 743 mm$^3$ and a second (upper) compartment having a volume of about 176 mm$^3$.

In some embodiments, the one or more solid ingredients may be aspirin, a statin, a menstrual pain reliever, an agent for increasing bone density, an agent for relieving hot flashes, CoQ10, a cholesterol reducer, a thyroid hormone, a bronchodilator (e.g. ephedrine sulfate), an expectorant, a decongestant (e.g. pseudoephedrine or guaifenesin), an anti-inflammatory agent (e.g. an NSAID), a prebiotic, a probiotic, a digestive enzyme, a stool softener, anti-platelet aggregation agent, a vitamin (e.g. vitamin D3 or vitamin E), a pain reliever, an isoflavone derivative (e.g. ipriflavone), medicinal herbs (e.g. cohosh or castus), a corticosteroid (e.g. dexamethasone), proton pump inhibitor, any other solid pharmaceutical agent, or a combination thereof.

In some embodiments, the one or more solid ingredients comprises a probiotic. The probiotic may be selected from the group consisting of *Lactobacillus acidophilus, Lactobacillus casei, Lactobacillus gasseri, Lactobacillus helveticus, Lactobacillus bulgaricus, Lactobacillus delbrueckii, Lactobacillus plantarum, Lactobacillus paracasei, Lactobacillus salivarius, Lactobacillus reuteri, Lactobacillus rhamnosus, Lactobacillus brevis, Lactobacillus breve, Streptococcus thermophilus, Bifidobacterium infantis, Bifidobacterium lactis, Bifidobacterium longum, Bifidobacterium bifidum, Bifidobacterium coagulans, Bifidobacterium breve, Bifidobacterium animalis, Bifidobacterium subtilis, Saccharomyces boulardi*, and combinations thereof. In some embodiments, the one or more solid ingredients comprises from about 1 million colony forming units (CFUs) to about 100 billion CFUs of a probiotic. In some embodiments, the one or more solid ingredients may comprise, for example, about 1 million CFUs of a probiotic, 50 million CFUs of a probiotic, 100 million CFUs of a probiotic, 200 million CFUs of a probiotic, 300 million CFUs of a probiotic, 400 million CFUs of a probiotic, 500 million CFUs of a probiotic, 600 million CFUs of a probiotic, 700 million CFUs of a probiotic, 800 million CFUs of a probiotic, 900 million CFUs of a probiotic, 1 billion CFUs of a probiotic, about 2 billion CFUs of a probiotic, about 3 billion CFUs of a probiotic, about 4 billion CFUs of a probiotic, about 5 billion CFUs of a probiotic, about 6 billion CFUs of a probiotic, about 7 billion CFUs of a probiotic, about 8 billion CFUs of a probiotic, about 9 billion CFUs of a probiotic, about 10 billion CFUs of a probiotic, about 11 billion CFUs of a probiotic, about 12 billion CFUs of a probiotic, about 13 billion CFUs of a probiotic, about 14 billion CFUs of a probiotic, about 15 billion CFUs of a probiotic, about 20 billion CFUs of a probiotic, about 30 billion CFUs of a probiotic, about 40 billion CFUs of a probiotic, about 50 billion CFUs of a probiotic, about 60 billion CFUs of a probiotic, about 70 billion CFUs of a probiotic, about 80 billion CFUs of a probiotic, about 90 billion CFUs of a probiotic, about 100 billion CFUs of a probiotic, or any range between any of these values, including endpoints.

In some embodiments, the one or more solid ingredients comprises a digestive enzyme. The digestive enzyme may be selected from the group consisting of amylase, alpha-amylase, protease, alpha-galactosidase, beta-gulcanase, galactomannase, lactase, lipase, cellulase, hemicellulase, phytase, sucrase, invertase, pectinase, maltase, malt diastase, glucoamylase, xylanase, pullulanase, peptidase and dipeptidyl peptidase IV, *serratia* peptidase, lysozyme, bromelian, papain, and combinations thereof. In some embodiments, the one or more solid ingredients comprises from about 10 mg to about 10000 mg of a digestive enzyme. In some embodiments, the one or more solid ingredients may comprise, for example, about 10 mg of a digestive enzyme, about 20 mg of a digestive enzyme, about 30 mg of a digestive enzyme, about 40 mg of a digestive enzyme, about 50 mg of a digestive enzyme, about 60 mg of a digestive enzyme, about 70 mg of a digestive enzyme, about 80 mg of a digestive enzyme, about 90 mg of a digestive enzyme, about 100 mg of a digestive enzyme, about 200 mg of a digestive enzyme, about 300 mg of a digestive enzyme, about 400 mg of a digestive enzyme, about 500 mg of a digestive enzyme, about 600 mg of a digestive enzyme, about 700 mg of a digestive enzyme, about 800 mg of a digestive enzyme, about 900 mg of a digestive enzyme, about 1000 mg of a digestive enzyme, or any range between any of these values, including endpoints.

In some embodiments, the first compartment comprises from about one million CFUs to about 100 billion CFUs of a probiotic, and the second compartment comprises from about 10 mg to about 1000 mg of a digestive enzyme. In some embodiments, the first compartment comprises from about 10 mg to about 1000 mg of a digestive enzyme, and the second compartment comprises from about 1 million CFUs to about 100 billion CFUs of a probiotic.

The compartment comprising the probiotic may have a volume of about 50 mm$^3$ to about 1000 mm$^3$, and the compartment comprising the digestive enzyme may have a volume of about 50 mm$^3$ to about 1000 mm$^3$.

In some embodiments, the one or more solid ingredients comprises a pharmaceutical agent. In some embodiments, the pharmaceutical agent is selected from, for example, aspirin, a statin, ipriflavone, cohosh, castus, coenzyme Q10 (CoQ10), guaifenesin, althea root, antimony pentasulfide, creosote, guaiacolsulfonate, ipecacuanha (syrup of ipecac), levoverbenone, potassium iodide, senega, tyloxapol, ammonium chloride, salbutamol, albuterol, levosalbutamol, levalbuterol, pseudoephedrine, dexamethasone, pirbuterol, epinephrine, ephedrine, terbutaline, salmeterol, clenbuterol, formoterol, bambuerol, indacaterol, ephrinesulfate, ticlopidine, clopidogrel, prasugrel, ticagrelor, cilostazol, vorapaxar, trifusal, dipyridamole, a tocotrienol, and combinations thereof.

In some embodiments, the one or more solid ingredients comprises aspirin. In some embodiments, the one or more solid ingredients comprises from about 10 mg to about 500 mg of aspirin. In some embodiments, the aspirin may be in an amount of about 50 mg to about 500 mg, about 100 mg to about 500 mg, about 150 mg to about 500 mg, about 200 mg to about 500 mg, about 50 mg to about 400 mg, about 100 mg to about 400 mg, about 150 mg to about 400 mg, about 200 mg to about 400 mg, or a range between any two of these values. In some embodiments, the aspirin comprises from about 81 mg to about 324 mg. In some embodiments, one of the first or second compartment comprises aspirin and the other compartment may comprise a statin. In some embodiments, the statin may be in an amount of about 1 mg to about 100 mg, about 1 mg to about 50 mg, about 1 mg to about 30 mg, about 1 mg to about 20 mg, about 1 mg to about 10 mg, about 10 mg to about 100 mg, about 20 mg to about 100 mg, about 30 mg to about 100 mg, about 50 mg to about 100 mg, about 75 mg to about 100 mg, about 1 mg, about 10 mg, about 25 mg, about 50 mg, about 75 mg, about 100 mg, or a range between any two of these values.

In some embodiments, the compartment comprising aspirin has a volume of about 50 mm$^3$ to about 1000 mm$^3$, and the other compartment has a volume of about 50 mm$^3$ to about 1000 mm$^3$.

In some embodiments, both compartments may comprise aspirin. For example, the first or second compartment may comprise about 300 mg of aspirin and the other compartment may comprise about 200 mg of aspirin.

In some embodiments, the first or second compartment may comprise aspirin, while the other compartment may comprise a statin, a vitamin D3, or a combination thereof.

In some embodiments, the one or more solid ingredients may be a cholesterol reducer, a pain reliever, an anti-platelet aggregation agent, or a combination thereof.

In some embodiments, the first or second compartment may comprise aspirin, while the other compartment may comprise ipriflavone, cohosh, castus, or a combination thereof.

In some embodiments, the first or second compartment may comprise aspirin, while the other compartment may comprise pseudoephedrine, dexamethasone or a combination thereof. In some embodiments, the pseudoephedrine may be in an amount of about 10 mg to about 500 mg, about 50 mg to about 500 mg, about 100 mg to about 500 mg, about 150 mg to about 500 mg, about 200 mg to about 500 mg, about 50 mg to about 400 mg, about 100 mg to about 400 mg, about 150 mg to about 400 mg, about 200 mg to about 400 mg, about 50 mg, about 100 mg, about 120 mg, about 140 mg, about 150 mg, about 200 mg, or a range between any two of these values. In some embodiments, the dexamethasone may be in an amount of about 5 mg to about 100 mg, about 5 mg to about 50 mg, about 10 mg to about 100 mg, about 10 mg to about 50 mg, about 5 mg to about 40 mg, about 10 mg to about 40 mg, about 5 mg, about 10 mg, about 15 mg, about 20 mg, about 25 mg, about 30 mg, about 35 mg, about 40 mg, or a range between any two of these values. For example, the first or second compartment may comprise about 500 mg aspirin and the other compartment may comprise about 120 mg of pseudoephedrine and about 10 mg to about 40 mg of dexamethasone.

In some embodiments, the first or second compartment may comprise naproxen and the other compartment may comprise pseudoephedrine. In some embodiments, the naproxen is in an amount of about 10 mg to about 500 mg, about 50 mg to about 500 mg, about 100 mg to about 500 mg, about 150 mg to about 500 mg, about 200 mg to about 500 mg, about 50 mg to about 400 mg, about 100 mg to about 400 mg, about 150 mg to about 400 mg, about 200 mg to about 400 mg, about 50 mg to about 300 mg, about 100 mg to about 300 mg, about 150 mg to about 300 mg, about 200 mg to about 300 mg, about 50 mg, about 100 mg, about 150 mg, about 200 mg, about 250 mg, about 300 mg, or a range between any two of these values. For example, in some embodiments, the first or second compartment may comprise about 300 mg of naproxen and the other compartment may comprise about 120 mg of pseudoephedrine. In some embodiments, the first or second compartment may comprise aspirin and the other compartment may comprise a proton pump inhibitor. In some embodiments, the proton pump inhibitor may be selected from omeprazole, lansoprazole, dexlansoprazole, rabeprazole, pantoprazole, esomeprazole, or a combination thereof. In some embodiments, the proton pump inhibitor may be in an amount of about 5 mg to about 100 mg, about 10 mg to about 100 mg, about 15 mg to about 100 mg, about 20 mg to about 100 mg, about 25 mg to about 100 mg, about 30 mg to about 100 mg, about 5 mg to about 50 mg, about 10 mg to about 50 mg, about 15 mg to about 50 mg, about 20 mg to about 50 mg, about 25 mg to about 50 mg, about 30 mg to about 50 mg, about 5 mg to about 30 mg, about 10 mg to about 30 mg, about 15 mg to about 30 mg, about 20 mg to about 30 mg, about 25 mg to about 30 mg, about 5 mg, about 10 mg, about 15 mg, about 20 mg, about 25 mg, about 30 mg, about 35 mg, about 40 mg, about 45 mg, about 50 mg, or a range between any two of these values. For example, in some embodiments, the first or second compartment may comprise about 500 mg aspirin and the other compartment may comprise about 30 mg of a proton pump inhibitor. In some embodiments, the one or more solid ingredients may be a menstrual pain reliever, an agent for increasing bone density, an agent for relieving hot flashes, or a combination thereof. In some embodiments, the first or second compartment may comprise a statin, and the other compartment may comprise CoQ10, aspirin, or a combination thereof. In some embodiments, the one or more solid ingredients may be a cholesterol reducer, CoQ10, or a combination thereof. In some embodiments, the first or second compartment may comprise guaifesnesin, and the other compartment may comprise ephrinesulfate. In some embodiments, the one or more solid ingredients include a bronchodilator and an expectorant. In some embodiments, the first or second compartment may comprise a prebiotic for gut health and a stool softener. In some embodiments, the first or second compartment may comprise a prebiotic and the other compartment may comprise docusate.

In some embodiments, the first or second compartment comprises aspirin and the other compartment comprises ticlopidine. In some embodiments, the one or more solid ingredients is an anti-platelet aggregation agent, aspirin, and a combination thereof. In some embodiments, the first or second compartment comprises aspirin and the second compartment comprises a tocotrienol. In some embodiments, the one or more solid ingredients is in powder or beadlet form.

In some embodiments, the one or more solid ingredients comprises a statin. The statin may be selected from the group consisting of atorvastatin, fluvastatin, lovastatin, pitavastatin, pravastatin, rosuvastatin, simvastatin, and combinations thereof. The statin may be in an amount of about 1 mg to about 100 mg. In some embodiments, the statin may be in an amount of about 1 mg, about 10 mg, about 20 mg, about 30 mg, about 40 mg, about 50 mg, about 100 mg, or a range between any two of these values. In some embodiments, the statin may be in an amount of about 5 mg to about 40 mg. In some embodiments, one of the first or second compartments comprises a statin in an amount of about 1 mg to about 100 mg. In some embodiments, the other compartment may comprise a second ingredient, such as, for example, aspirin, triiodothyronine, a statin, a probiotic, a digestive enzyme, or combinations thereof.

In some embodiments, the compartment comprising a statin has a volume of about 50 mm$^3$ to about 1000 mm$^3$, and the other compartment has a volume of about 50 mm$^3$ to about 1000 mm$^3$.

In some embodiments, the first compartment may comprise from about 10 mg to about 500 mg of aspirin, and the second compartment may comprise from about 10 mg to about 500 mg of ipriflavone, about 1 mg to about 150 mg of cohosh, about 10 mg to about 1000 mg of castus, or any combination thereof. In some embodiments the ipriflavone may be in an amount of about 10 mg to about 1000 mg. In some embodiments, the ipriflavone may be in an amount of about 50 mg, about 100 mg, about 200 mg, about 300 mg, about 400 mg, about 500 mg, about 600 mg, about 700 mg, about 800 mg, about 900 mg, about 1000 mg, or a range between any two of these values. In some embodiments the cohosh may be in an amount of about 1 mg to about 150 mg. In some embodiments, the cohosh may be in an amount of about 1 mg, about 10 mg, about 20 mg, about 30 mg, about 40 mg, about 50 mg, about 100 mg, about 150 mg, or a range between any two of these values. In some embodiments the castus may be in an amount of about 10 mg to about 1000 mg. In some embodiments, the castus may be in an amount of about 50 mg, about 100 mg, about 200 mg, about 300 mg, about 400 mg, about 500 mg, about 600 mg, about 700 mg, about 800 mg, about 900 mg, about 1000 mg, or a range between any two of these values.

In some embodiments, the first compartment may comprise from about 1 mg to about 100 mg of a statin, and the second compartment may comprise from about 10 mg to about 500 mg of aspirin, about 10 mg to about 1000 mg of CoQ10, or any combination thereof. In some embodiments the CoQ10 may be in an amount of about 10 mg to about 1000 mg. In some embodiments, the CoQ10 may be in an amount of about 50 mg, about 100 mg, about 200 mg, about 300 mg, about 400 mg, about 500 mg, about 600 mg, about 700 mg, about 800 mg, about 900 mg, about 1000 mg, or a range between any two of these values.

In some embodiments, the first compartment may comprise from about 10 mg to about 1200 mg of an expectorant, and the second compartment may comprise from about 5 mg to about 150 mg of a bronchodilator. In some embodiments the expectorant may be in an amount of about 10 mg to about 1000 mg. In some embodiments, the expectorant may be in an amount of about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, or a range between any two of these values. In some embodiments the bronchodilator may be in an amount of about 10 mg to about 150 mg. In some embodiments, the bronchodilator may be in an amount of about 10 mg, about 20 mg, about 30 mg, about 40 mg, about 50 mg, about 100 mg, about 150 mg, or a range between any two of these values. In some embodiments, the expectorant may be, for example, guaifenesin, althea root, antimony pentasulfide, creosote, guaiacolsulfonate, ipecacuanha (syrup of ipecac), levoverbenone, potassium iodide, senega, tyloxapol, ammonium chloride, or any combination thereof. In some embodiments, the bronchodilator may be, for example, salbutamol, albuterol, levosalbutamol, levalbuterol, pirbuterol, epinephrine, ephedrine, terbutaline, salmeterol, clenbuterol, formoterol, bambuerol, indacaterol, ephrinesulfate, or any combination thereof.

In some embodiments, the first or second compartment comprises a non-steroidal anti-inflammatory drug (NSAID) and the other compartment comprises a proton pump inhibitor. In some embodiments the NSAID may be in an amount of about 10 mg to about 1000 mg. In some embodiments, the NSAID may be in an amount of about 50 mg, about 100 mg, about 200 mg, about 300 mg, about 400 mg, about 500 mg, about 600 mg, about 700 mg, about 800 mg, about 900 mg, about 1000 mg, or a range between any two of these values. In some embodiments, the NSAID may be selected from aspirin, ibuprofen, naproxen, diflunisal, salicylic acid and other salicylates, salsalate, dexibuprofen, fenoprofen, ketoprofen, dexketoprofen flurbiprofen, oxaprozin, loxoprofen, acetic acid derivatives, indomethacin, tolmetin, sulindac, etodolac, ketorolac, diclofenac, aceclofenac, nabumetone, enolic acid, piroxicam, meloxicam, tenoxicam, droxicam, lornoxicam, isoxicam, phenylbutazone, anthranilic acid derivatives, mefenamic acid, meclofenamic acid, flufenamic acid, tolfenamic acid, celecoxib, rofecoxib, valdecoxib, parecoxib, lumiracoxib, etoricoxib, firocoxib, sulfonanilides, nimesulide, clonixin, licofelone, H-harpagide, or a combination thereof.

In some embodiments, the first compartment may comprise from about 1 million CFUs to about 100 billion CFUs of a probiotic, and the second compartment may comprise from about 10 mg to about 500 mg of a stool softener. In some embodiments, the stool softener may be, for example, docusate.

In some embodiments, the first compartment may comprise from about 10 mg to about 500 mg of aspirin, and the second compartment may comprise from about 10 mg to about 500 mg of a platelet aggregation inhibitor. In some embodiments, the platelet aggregation inhibitor may be, for example, ticlopidine, clopidogrel, prasugrel, ticagrelor, cilostazol, vorapaxar, trifusal, dipyridamole, or any combination thereof.

In some embodiments, the first compartment may comprise from about 10 mg to about 500 mg of aspirin, and the second compartment may comprise from about 10 mg to about 500 mg of a form or derivative of vitamin E. In some embodiments, the form or derivative of vitamin E may be a tocotrienol, such as, for example, alpha tocotrienol, beta tocotrienol, gamma tocotrienol, delta tocotrienol, or any combination thereof.

Table 1 below lists some possible combinations of solid ingredients which may be found in some embodiments. It is to be understood that any of the ingredients within Table 1 may be found in any combination, and may be found in either compartment of the capsule described herein. It is to be further understood that the embodiments described in Table 1 are not meant to be limiting, but are merely illustrative.

TABLE 1

| First compartment | Second compartment |
|---|---|
| About 1 million to about 100 billion CFUs of a probiotic | About 10 mg to about 1000 mg of a digestive enzyme |
| About 10 mg to about 500 mg of aspirin | About 1 mg to about 100 mg of a statin |
| About 10 mg to about 500 mg of aspirin | About 10 mg to about 500 mg of ipriflavone, and/or about 1 mg to about 150 mg of cohosh, and/or about 10 mg to about 1000 mg of castus |
| About 1 mg to about 100 mg of a statin | About 10 mg to about 500 mg of aspirin and/or about 10 mg to about 1000 mg of CoQ10 |
| About 10 mg to about 1200 mg of an expectorant | About 5 mg to about 150 mg of a bronchodilator |
| About 1 million to about 100 billion CFUs of a probiotic | About 10 mg to about 500 mg of a stool softener |
| About 10 mg to about 500 mg of aspirin | About 10 mg to about 500 mg of a platelet aggregation inhibitor |
| About 10 mg to about 500 mg of aspirin | About 10 mg to about 500 mg of a form or derivative of vitamin E |
| About 10 mg to about 500 mg of aspirin | About 10 mg to about 500 mg of aspirin |
| About 10 mg to about 500 mg of aspirin | About 10 mg to about 300 mg of pseudoephedrine; and/or About 10 mg to about 100 mg of dexmethylphenidate |
| About 10 mg to about 500 mg of naproxen | About 10 mg to about 300 mg of pseudoephedrine |
| About 10 mg to about 500 mg of aspirin | About 10 mg to about 100 mg of a proton pump inhibitor |
| About 10 mg to about 1000 mg of a non-steroidal anti-inflammatory drug (NSAID) | About 10 mg to about 100 mg of a proton pump inhibitor |

One skilled in the art would understand that the above examples are not meant to be limiting, but are illustrative of the types of ingredients that can be included in the compartments. In the examples above, the ingredient(s) in the first compartment may be in the second compartment, instead, and vice versa.

The method of making the type of multi-compartment capsule described herein differs from methods typically used in the art because in the present capsule, the diaphragm is bonded or fitted to the body of the capsule, effectuating a sealed compartment between the lower end of the body and the outer surface of the diaphragm, thus separating the first compartment from the second compartment and preventing leakage or spillage. Additionally, for example, in a typical capsule-in-capsule design, the outer capsule's dry ingredients cannot be displaced in order to make a place for an inner capsule. The inner capsule will simply sit on top of the powder and leave insufficient space for recapping, or worse, be crushed because of the powder's inability to be displaced. Further, the dosing of the powder in a typical capsule-in-capsule design (dose after capsule insertion) makes it extremely challenging to dose the powder between the sidewalls (especially with a size 1 capsule).

Table 2 below shows various dimensions of standard and elongated TORPAC capsule sizes, which may be used in some embodiments described herein.

TABLE 2

| | CAPSULE SIZE | | | | | | | | | |
|---|---|---|---|---|---|---|---|---|---|---|
| | 000 | 00E | 00 | 00LQ | 0E | 0 | 1 | 2 | 3 | 4 |
| WEIGHT | | | | | | | | | | |
| Average Weight (mg) | 158 | 130 | 123 | 132 | 107 | 99 | 76 | 61 | 48 | 38 |
| tolerance | ±10 | ±10 | ±7 | ±4 | ±7 | ±6 | ±5 | ±4 | ±3 | ±3 |
| CAPACITY | | | | | | | | | | |
| Volume Capacity (ml) | 1.37 | 1.02 | 0.95 | 0.95 | 0.77 | 0.68 | 0.48 | 0.36 | 0.27 | 0.20 |
| density of dosing powder | | | | | Weight Capacity (mg) | | | | | |
| 0.6 g/ml | 822 | 612 | 570 | 570 | 462 | 408 | 288 | 216 | 162 | 120 |
| 0.8 g/ml | 1096 | 816 | 760 | 760 | 616 | 544 | 384 | 288 | 216 | 160 |
| 1.0 g/ml | 1370 | 1020 | 950 | 950 | 770 | 680 | 480 | 360 | 270 | 200 |
| 1.2 g/ml | 1644 | 1224 | 1140 | 1140 | 924 | 816 | 576 | 432 | 324 | 240 |
| OVERALL CLOSED LENGTH | | | | | | | | | | |
| (mm) | 26 | 25.4 | 23.4 | 23.4 | 23.4 | 21.6 | 19.4 | 17.6 | 15.7 | 14.3 |
| tolerance | ±0.3 | ±0.3 | ±0.3 | ±0.3 | ±0.3 | ±0.3 | ±0.3 | ±0.3 | ±0.3 | ±0.3 |
| (inches) | 1.024 | 1 | 0.921 | 0.921 | 0.921 | 0.85 | 0.764 | 0.693 | 0.618 | 0.563 |
| tolerance | ±0.012 | ±0.012 | ±0.012 | ±0.012 | ±0.012 | ±0.012 | ±0.012 | ±0.012 | ±0.012 | ±0.012 |
| INDIVIDUAL LENGTHS (CAP & BODY) | | | | | | | | | | |
| CAP (mm) | 12.9 | 12.94 | 11.8 | 11.8 | 11.9 | 10.85 | 9.85 | 8.8 | 8 | 7.2 |
| tolerance | ±0.35 | ±0.35 | ±0.35 | ±0.35 | ±0.35 | ±0.35 | ±0.35 | ±0.35 | ±0.35 | ±0.35 |
| BODY (mm) | 21.9 | 22.38 | 20.1 | 20.1 | 20 | 18.45 | 16.4 | 15.15 | 13.45 | 12.1 |
| tolerance | ±0.35 | ±0.35 | ±0.35 | ±0.35 | ±0.35 | ±0.35 | ±0.35 | ±0.35 | ±0.35 | ±0.35 |
| CAP (inches) | 0.508 | 0.509 | 0.464 | 0.464 | 0.468 | 0.427 | 0.388 | 0.346 | 0.315 | 0.283 |
| tolerance | ±0.014 | ±0.014 | ±0.014 | ±0.014 | ±0.014 | ±0.014 | ±0.014 | ±0.014 | ±0.014 | ±0.014 |
| BODY (inches) | 0.862 | 0.881 | 0.791 | 0.791 | 0.787 | 0.726 | 0.646 | 0.596 | 0.529 | 0.476 |
| tolerance | ±0.014 | ±0.014 | ±0.014 | ±0.014 | ±0.014 | ±0.014 | ±0.014 | ±0.014 | ±0.014 | ±0.014 |

TABLE 2-continued

| | CAPSULE SIZE | | | | | | | | | |
|---|---|---|---|---|---|---|---|---|---|---|
| | 000 | 00E | 00 | 00LQ | 0E | 0 | 1 | 2 | 3 | 4 |
| EXTERNAL DIAMETER | | | | | | | | | | |
| CAP (mm) | 9.94 | 8.58 | 8.56 | 8.56 | 7.66 | 7.65 | 6.96 | 6.39 | 5.85 | 5.33 |
| BODY (mm) | 9.55 | 8.25 | 8.23 | 8.23 | 7.35 | 7.35 | 6.63 | 6.12 | 5.60 | 5.08 |
| CAP (inches) | 0.391 | 0.338 | 0.337 | 0.337 | 0.302 | 0.301 | 0.274 | 0.252 | 0.23 | 0.21 |
| BODY (inches) | 0.376 | 0.325 | 0.324 | 0.324 | 0.289 | 0.289 | 0.261 | 0.241 | 0.22 | 0.2 |

Recommended Storage Conditions:
59°-77° F./15°-25 °C.
RH 35-65%

Table 3 below shows additional dimensions of standard and elongated TORPAC capsule sizes, which may be used in some embodiments described herein.

TABLE 3

| | Typical Fill Weights (mg) Actual Fill Weights may vary and depend on powder characteristics Powder Density | | | Volume Theoretical (ml) | Locked Length +/−0.76 (mm) | Tolerance Component | External Diam. (mm) | Cut Length +/−0.51 (mm) | Single Wall Thickness +/−0.03 (mm) | Weight (Avg. of 100) +/− 10% (mg) |
|---|---|---|---|---|---|---|---|---|---|---|
| Size | 0.45 Light | 0.70 Typical | 1.00 Heavy | | | | | | | |
| 000 | 615 | 960 | 1370 | 1.37 | 26.14 | Cap | 9.91 | 12.95 | 0.112 | 163 |
| | | | | | | Body | 9.55 | 22.20 | 0.110 | |
| 00 | 430 | 665 | 950 | 0.95 | 23.30 | Cap | 8.53 | 11.74 | 0.109 | 118 |
| | | | | | | Body | 8.18 | 20.22 | 0.107 | |
| 0 | 305 | 475 | 680 | 0.68 | 21.70 | Cap | 7.65 | 10.72 | 0.107 | 96 |
| | | | | | | Body | 7.34 | 18.44 | 0.104 | |
| 1 | 225 | 350 | 500 | 0.50 | 19.40 | Cap | 6.91 | 9.78 | 0.104 | 76 |
| | | | | | | Body | 6.63 | 16.61 | 0.102 | |
| 2 | 165 | 260 | 370 | 0.37 | 18.00 | Cap | 6.35 | 8.94 | 0.102 | 61 |
| | | | | | | Body | 6.07 | 15.27 | 0.099 | |
| 3 | 135 | 210 | 300 | 0.30 | 15.90 | Cap | 5.82 | 8.08 | 0.092 | 48 |
| | | | | | | Body | 5.56 | 13.59 | 0.890 | |
| 4 | 95 | 145 | 210 | 0.21 | 14.30 | Cap | 5.31 | 7.21 | 0.096 | 38 |
| | | | | | | Body | 5.05 | 12.19 | 0.091 | |
| 5 | 60 | 90 | 130 | 0.13 | 11.10 | Cap | 4.91 | 6.20 | 0.089 | 28 |
| | | | | | | Body | 4.68 | 9.32 | 0.086 | |

Although the present invention has been described in considerable detail with reference to certain preferred embodiments thereof, other versions are possible. Therefore, the spirit and scope of the appended claims should not be limited to the description and the preferred versions contained within this specification. Modifications and improvements to the disclosed embodiments will be apparent to those skilled in the art in light of this disclosure, and are intended to fall within the scope of the pending claims.

The invention claimed is:

1. A multi-compartment capsule comprising:
   a body;
   a diaphragm having a bottom and two sidewalls extending from the bottom and defining a top edge, the diaphragm extending into the body and forming a first compartment defined by a first surface of the diaphragm and the body; and
   a cap mounted to the body and opposed to the diaphragm, the cap forming a second compartment defined by an opposing surface of the diaphragm and the cap;
   wherein the two sidewalls of the diaphragm extend along and contact the inner surface of the body and the top edge is flush with an open end of the body, forming a seal between the diaphragm and the body;
   wherein the first compartment and the second compartment each contain one or more powders; and
   wherein the multi-compartment capsule is a size 00 capsule.

2. The capsule of claim 1, wherein the first compartment is hermetically sealed.

3. The capsule of claim 1, wherein the one or more powders comprises an aspirin, a statin, a menstrual pain reliever, an agent for increasing bone density, an agent for relieving hot flashes, coenzyme Q10 (CoQ10), a cholesterol reducer, a thyroid hormone, a bronchodilator, an expectorant, a decongestant, an anti-inflammatory agent, a prebiotic, a probiotic, a digestive enzyme, a stool softener, anti-platelet aggregation agent, a platelet aggregation inhibitor, a vitamin, vitamin E, vitamin D3, a pain reliever, an isoflavone derivative, medicinal herbs, a corticosteroid, a proton pump inhibitor, a pharmaceutical agent, a nonsteroidal anti-inflammatory drug, or a combination thereof.

4. The capsule of claim 3, wherein the digestive enzyme is selected from the group consisting of amylase, alpha-amylase, protease, alpha-galactosidase, beta-gulcanase, galactomannase, lactase, lipase, cellulase, hemicellulase, phytase, sucrase, invertase, pectinase, maltase, malt diastase, glucoamylase, xylanase, pullulanase, peptidase and dipeptidyl peptidas IV, serratia peptidase, lysozyme, bromelian, papain, and combinations thereof.

5. The capsule of claim 3, wherein the pharmaceutical agent is selected from selected from the group consisting of aspirin, a statin, ipriflavone, cohosh, castus, coenzyme Q10 (CoQ10), gauifenesin, althea root, antimony pentasulfide, creosote, guaiacolsulfonate, ipecacuanha (syrup of ipecac), levoverbenone, potassium iodide, senega, tyloxapol, ammonium chloride, salbutamol, albuterol, levosalbutamol, levalbuterol, pirbuterol, epinephrine, ephedrine, terbutaline, salmeterol, clenbuterol, formoterol, bambuerol, indacaterol, ephrinesulfate, ticlopidine, clopidogrel, prasugrel, ticagrelor, cilostazol, vorapaxar, trifusal, dipyridamole, a tocotrienol, and combinations thereof.

6. The capsule of claim 3, wherein the statin is selected from the group consisting of atorvastatin, fluvastatin, lovastatin, pitavastatin, pravastatin, rosuvastatin, simvastatin, and combinations thereof.

7. The capsule of claim 3, wherein the probiotic is selected from the group consisting of selected from the group consisting of *Lactobacillus acidophilus, Lactobacillus casei, Lactobacillus gasseri, Lactobacillus helveticus, Lactobacillus bulgaricus, Lactobacillus delbrueckii, Lactobacillus plantarum, Lactobacillus paracasei, Lactobacillus salivarius Lactobacillus reuteri, Lactobacillus rhamnosus, Lactobacillus brevis, Lactobacillus breve, Streptococcus thermophilus, Bifidobacterium infantis, Bifidobacterium lactis, Bifidobacterium longum, Bifidobacterium bifidum, Bifidobacterium coagulans, Bifidobacterium breve, Bifidobacterium animalis, Bifidobacterium subtilis, Saccharomyces boulardi*, and combinations thereof.

8. The capsule of claim 1, wherein the one or more powders comprises from about 1 million colony forming units to about 100 billion colony forming units of a probiotic.

9. The capsule of claim 1, wherein the one or more powders comprises from about 10 mg to about 1000 mg of a digestive enzyme.

10. The capsule of claim 1, wherein the first compartment comprises from about 1 million colony forming units to about 100 billion colony forming units of a probiotic, and the second compartment comprises from about 10 mg to about 1000 mg of a digestive enzyme.

11. The capsule of claim 1, wherein the first compartment comprises from about 10 mg to about 1000 mg of a digestive enzyme, and the second compartment comprises from about 1 million colony forming units to about 100 billion colony forming units of a probiotic.

12. The capsule of claim 1, wherein the one or more powders comprises from about 10 mg to about 500 mg of aspirin.

13. The capsule of claim 1, wherein the one or more powders comprises from about 1 mg to about 100 mg of a statin.

14. The capsule of claim 1, wherein the one or more powders contained in the first compartment are not crushed to accommodate the diaphragm.

15. A multi-compartment capsule comprising:
a body;
a diaphragm having a bottom and two sidewalls, the two sidewalls extending along and contacting an inner surface of the body to form a seal therebetween, wherein a first compartment is defined by the body and a first surface of the diaphragm; and
a cap mounted to the body and opposed to the diaphragm, wherein a second compartment is defined by the cap and a second surface of the diaphragm,
wherein the first compartment and the second compartment each contain one or more solid ingredients.

* * * * *